United States Patent [19]
Loeffler

[11] Patent Number: 5,891,154
[45] Date of Patent: Apr. 6, 1999

[54] PASSIVE PERFUSION STENT DELIVERY SYSTEM

[75] Inventor: Joseph P. Loeffler, Mountain View, Calif.

[73] Assignee: Advanced Cardiovascular System, Inc., Santa Clara, Calif.

[21] Appl. No.: 851,111

[22] Filed: May 6, 1997

[51] Int. Cl.⁶ .............................. A61F 11/00; A61M 29/00
[52] U.S. Cl. ........................... 606/108; 606/198; 606/194
[58] Field of Search ....................... 606/1, 108, 191–200; 623/1, 11, 12

[56] References Cited

U.S. PATENT DOCUMENTS

| | | |
|---|---|---|
| 4,661,094 | 4/1987 | Simpson . |
| 4,771,777 | 9/1988 | Horzewski et al. . |
| 4,790,315 | 12/1988 | Mueller, Jr. et al. . |
| 5,137,513 | 8/1992 | McInnes et al. . |
| 5,158,548 | 10/1992 | Lau et al. . |
| 5,195,971 | 3/1993 | Sirhan . |
| 5,222,971 | 6/1993 | Willard et al. . |
| 5,242,399 | 9/1993 | Lau et al. . |
| 5,279,562 | 1/1994 | Sirhan et al. . |
| 5,334,154 | 8/1994 | Samson et al. . |
| 5,368,566 | 11/1994 | Crocker . |
| 5,391,172 | 2/1995 | Williams et al. ........................ 606/108 |
| 5,458,615 | 10/1995 | Klemm et al. . |

FOREIGN PATENT DOCUMENTS

| | | |
|---|---|---|
| 0 442 657 A | 8/1991 | European Pat. Off. . |
| 0 505 686 A | 9/1992 | European Pat. Off. . |

*Primary Examiner*—Glenn K. Dawson
*Attorney, Agent, or Firm*—Fulwider Patton Lee & Utecht, LLP

[57] ABSTRACT

A stent delivery method and system are disclosed. The system generally includes an elongated delivery sheath and a perfusion catheter disposed within a sheath lumen of the sheath having an expandable member on its distal extremity. The sheath includes perfusion ports to maintain blood flow to perfusion ports in the catheter during delivery of the stent. A manipulating device is provided at the proximal end of the delivery system to effect relative axial movement between the sheath and the catheter so as to expose the stent mounted on the expandable member on the catheter within a body lumen such as a coronary artery and allow the expansion of the stent by the expansion of the expandable member.

12 Claims, 5 Drawing Sheets

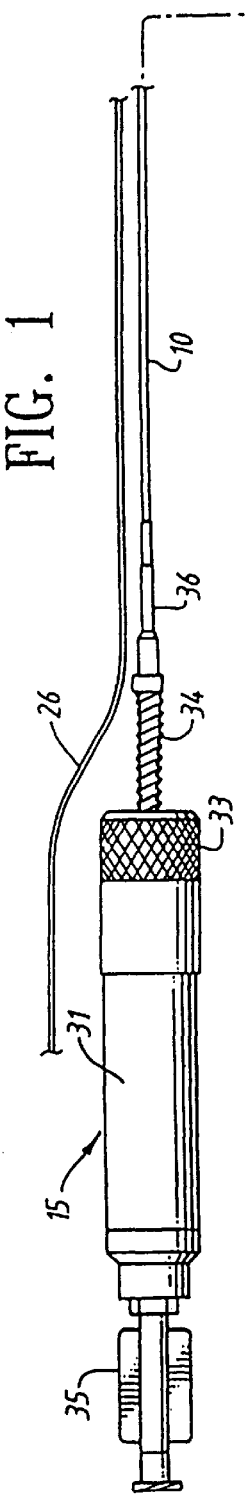
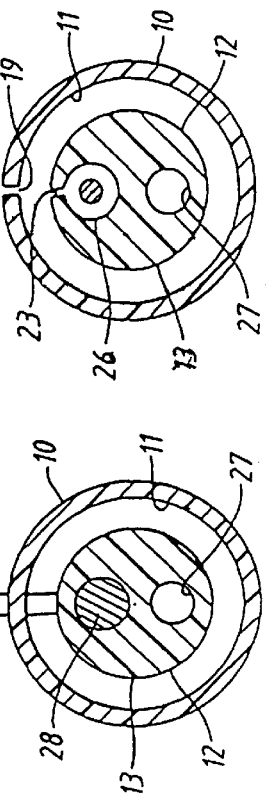
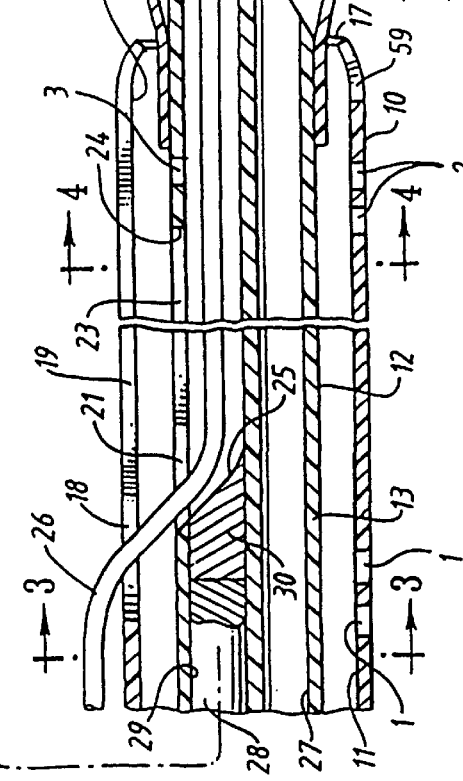
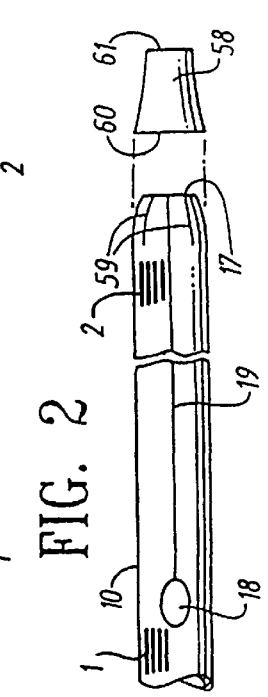
FIG. 1
FIG. 2
FIG. 3
FIG. 4

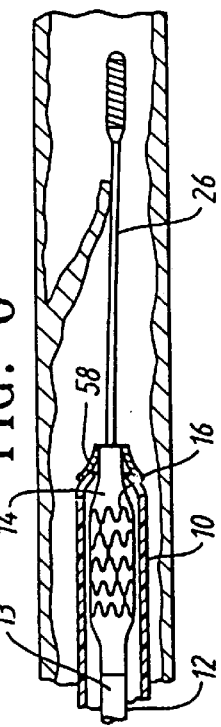
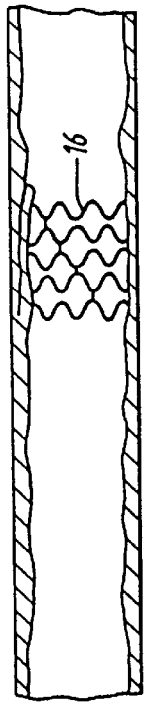
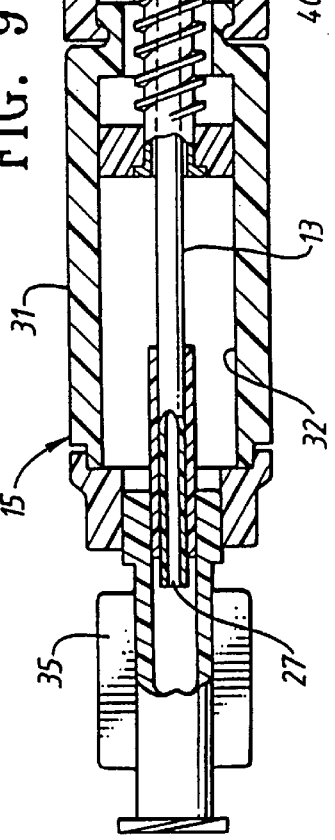
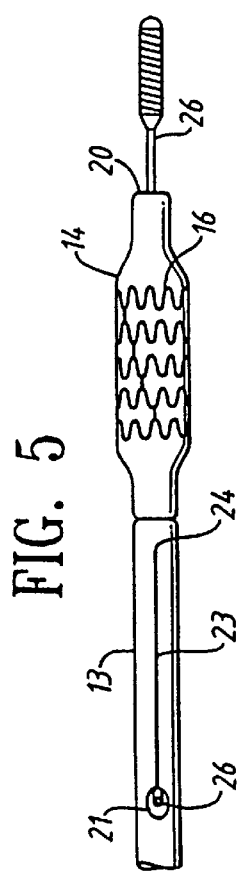
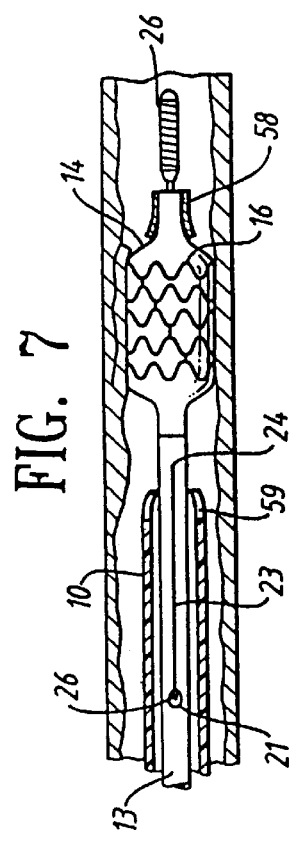

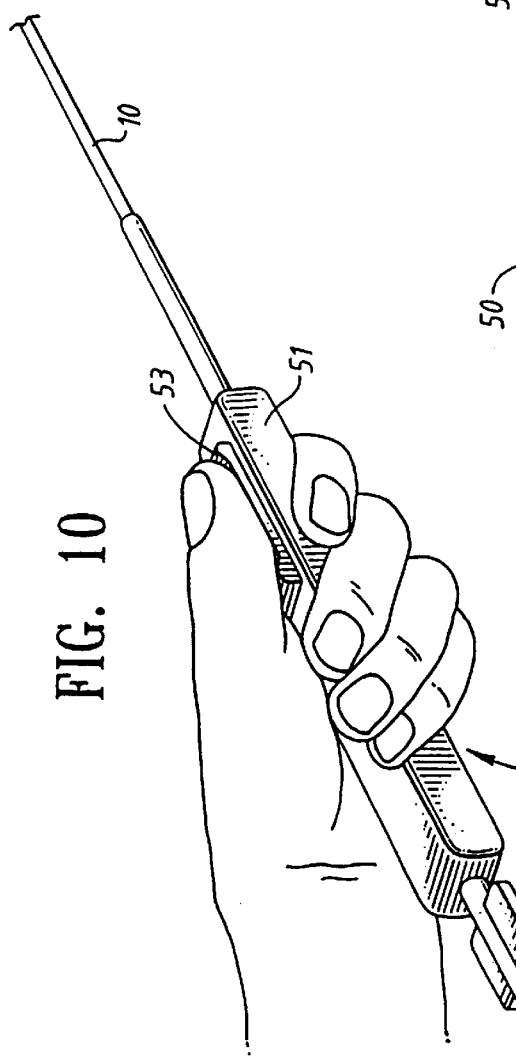
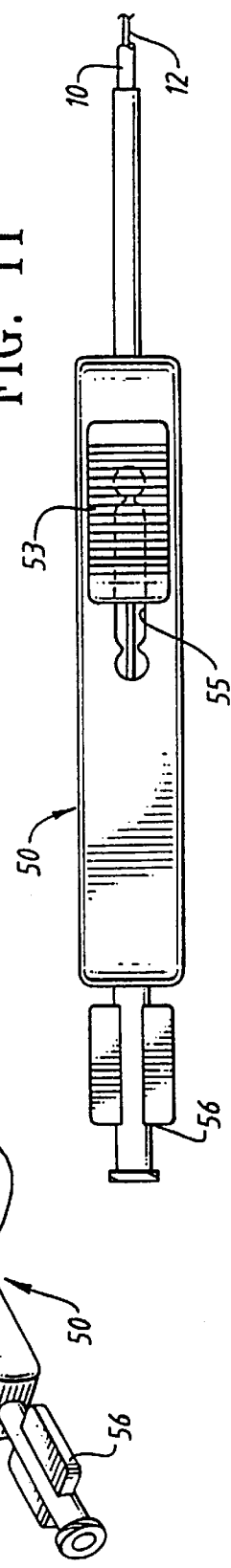
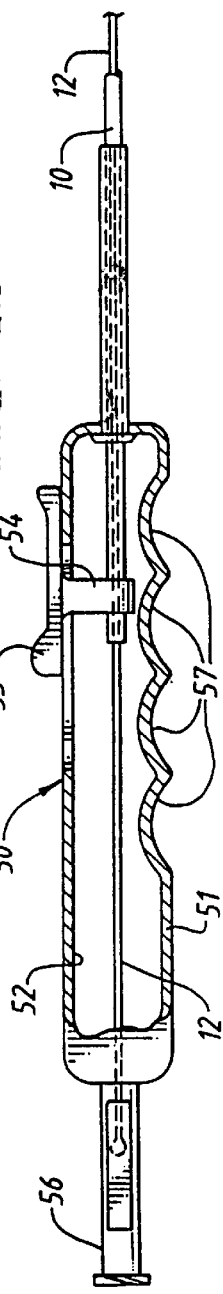

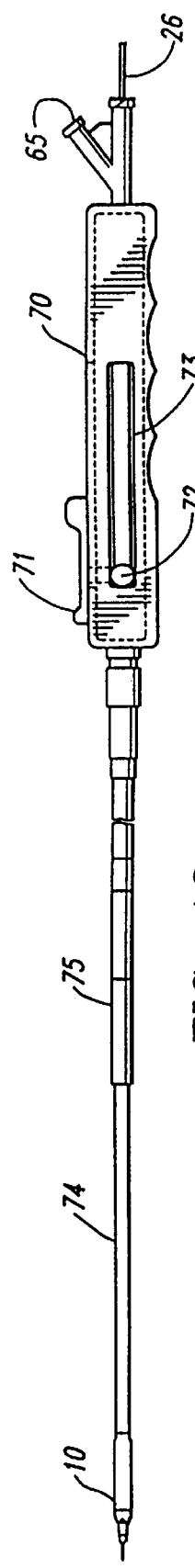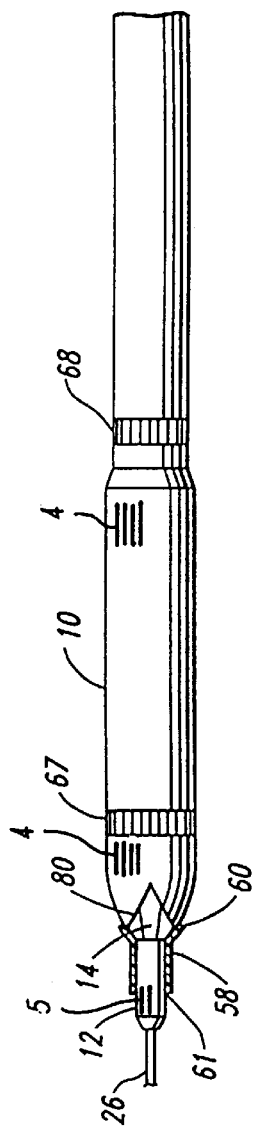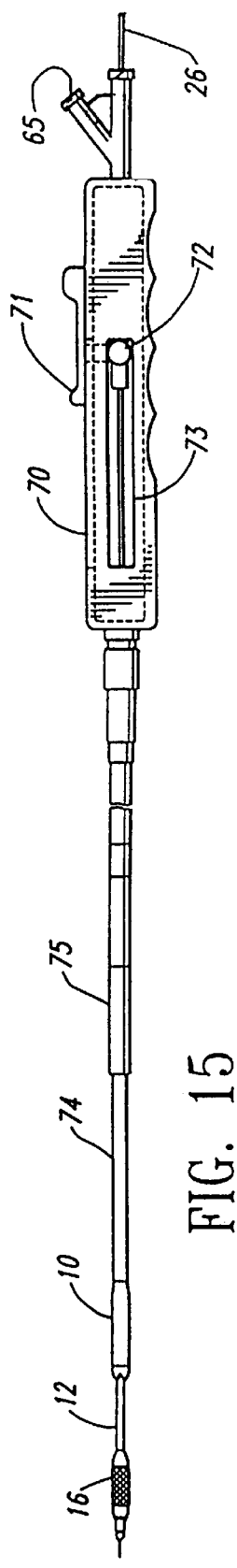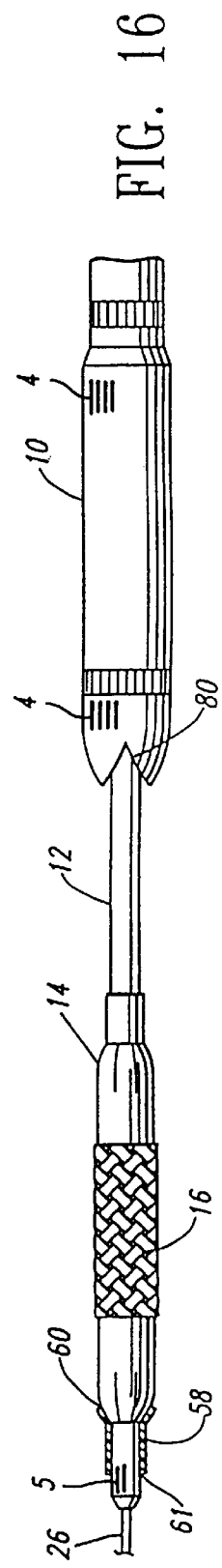

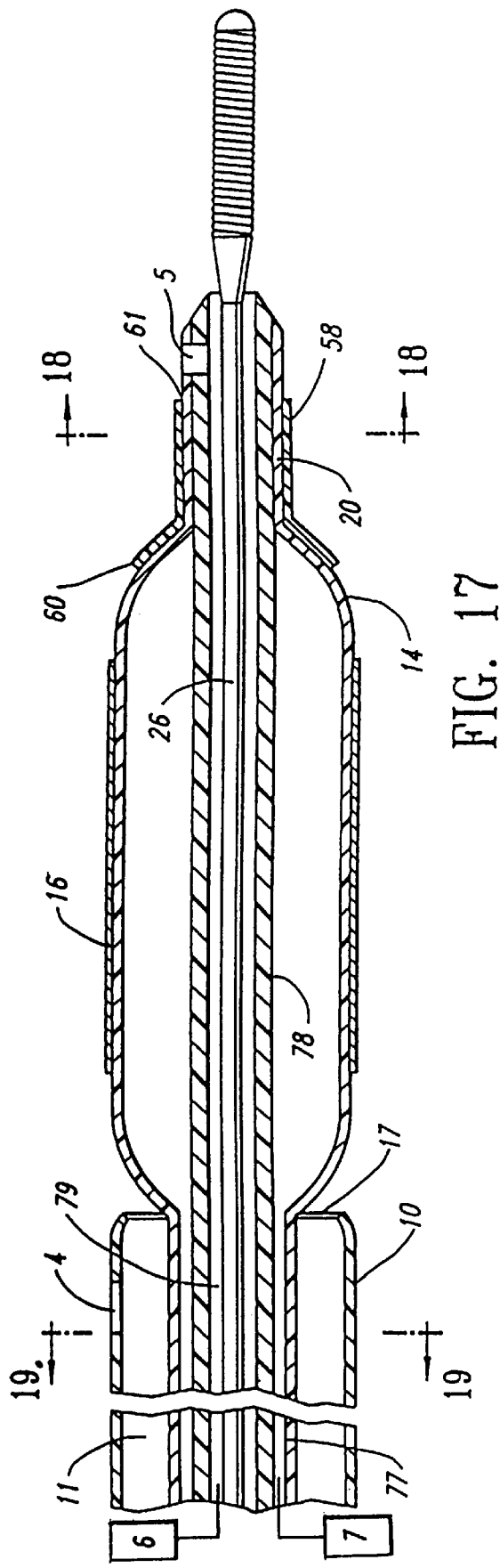
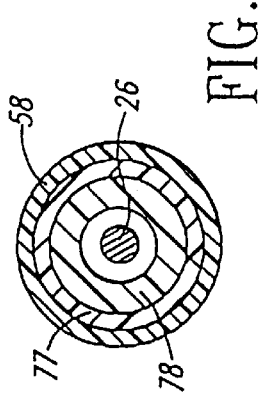
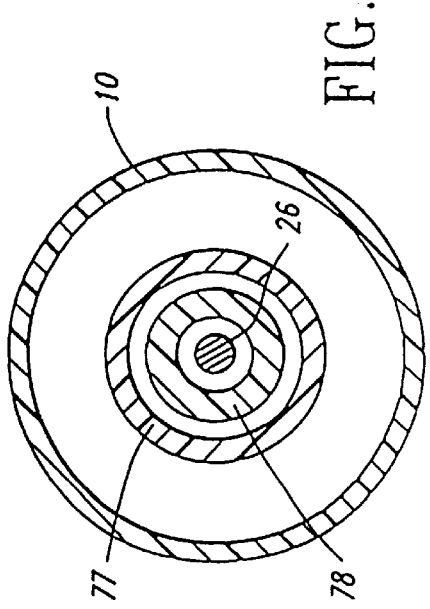
FIG. 17
FIG. 18
FIG. 19

PASSIVE PERFUSION STENT DELIVERY SYSTEM

BACKGROUND OF THE INVENTION

This invention relates to devices for the treatment of heart disease and particularly to endoarterial prosthesis, which are commonly called stents.

Several interventional treatment modalities are presently used for heart disease including balloon and laser angioplasty, atherectomy, and by-pass surgery. In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion.

Once in position across the lesion, the balloon which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom.

Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); and U.S. Pat. No. 4,748,982 (Horzewski, et al.) which are hereby incorporated herein in their entirety by reference thereto.

A major problem which can occur during balloon angioplasty procedures is the formation of intimal flaps which can collapse and occlude the artery when the balloon is deflated at the end of the angioplasty procedure. Another major problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient is put in an extremely dangerous situation requiring immediate medical attention, particularly in the coronary arteries.

A major focus of recent development work in the treatment of heart disease has been directed to endoprosthetic devices called stents. Stents are generally cylindrically shaped intravascular devices which are placed within a damaged artery to hold it open. The device can be used to prevent restenosis and to maintain the patency of blood vessel immediately after intravascular treatments. In some circumstances, they can also be used as the primary treatment device where they are expanded to dilate a stenosis and then left in place.

But the rapid and effective delivery of a stent to the desire location within the patient's vasculature has been found to be difficult, particularly in those situations in which an intimal flap has occluded an artery. Attempts to advance a stent into regions of coronary arteries occluded by dissected arterial linings have not been very successful.

The two basic methods and systems have been developed for delivering stents to desired locations within body lumens. One method and system involves compressing or otherwise reducing the diameter of an expandable stent, disposing the compressed stent within a lumen provided in the distal end of a tubular catheter, advancing the catheter through the patient's vasculature until the distal end of the catheter is immediately adjacent to the desired vascular location and then pushing the stent out the distal end of the catheter into the desired location. Once out of the catheter, the compressed stent expands or is expanded to thereby hold open the artery or other body lumen into which it is placed.

Another method and system involves disposing a compressed or otherwise small diameter stent about an expandable member such as a balloon on the distal end of a catheter, advancing the catheter through the patient's vascular system until the stent is in the desired location within a blood vessel and then expanding the expandable member on the catheter to expand the stent within the blood vessel. The expanded expandable member is then contracted and the catheter withdrawn, leaving the expanded stent within the blood vessel, holding open the passageway thereof.

The following references illustrate various types of stents and stent delivery systems. The list is meant to be exemplary, not exhaustive on the subject.

| | |
|---|---|
| U.S. Pat. No. 3,868,956 | U.S. Pat. No. 4,503,569 |
| U.S. Pat. No. 4,512,338 | U.S. Pat. No. 4,553,545 |
| U.S. Pat. No. 4,560,374 | U.S. Pat. No. 4,655,771 |
| U.S. Pat. No. 4,665,918 | U.S. Pat. No. 4,733,665 |
| U.S. Pat. No. 4,760,849 | U.S. Pat. No. 4,762,128 |
| U.S. Pat. No. 4,768,507 | U.S. Pat. No. 4,795,458 |
| U.S. Pat. No. 4,800,882 | U.S. Pat. No. 4,830,003 |
| U.S. Pat. No. 4,856,516 | U.S. Pat. No. 4,878,906 |
| U.S. Pat. No. 4,886,062 | U.S. Pat. No. 4,907,336 |
| U.S. Pat. No. 4,913,141 | U.S. Pat. No. 4,923,464 |
| U.S. Pat. No. 4,950,227 | U.S. Pat. No. 5,458,615 |

What has been needed and heretofore unavailable is a stent delivery system which can be quickly and easily used in a wide variety of situations and particularly in emergency situations where a dissected arterial lining has collapsed and has occluded the flow of blood to a vital organ. The present invention satisfies this need.

In addition, because the expandable member such as a balloon is inflated, the flow of blood in the artery or vessel being treated is occluded. The balloon can only be inflated for a limited amount of time, typically on the order of 15 to 60 seconds. A longer inflation time would be desirable because it would: allow more time for the surgeon to deploy the stent; allow maximum stent to vessel conformity; and permit good artery seating of the stent. On the other hand, risks of prolonged balloon inflation time include angina or ischemic conditions in tissue distal to the catheter.

The importance of continuous blood flow during percutaneous transluminal coronary or peripheral vascular applications is recognized. Indeed, a perfusion-type dilatation catheter for angioplasty was introduced into the marketplace by Advanced Cardiovascular Systems, Inc. (ACS). This catheter, which can take the form of an over-the-wire, a fixed wire, or a rapid exchange type catheter, has one or more perfusion ports proximal and one or more perfusion ports distal to the dilatation balloon, which ports are in fluid communication with a guidewire receiving inner lumen extending to the distal end of the catheter. When the balloon is inflated to dilate a stenosis, oxygenated blood in the artery or aorta, or both, is forced through the proximal perfusion ports, through the inner lumen of the catheter, and out of the distal perfusion ports.

The rapid exchange version of the perfusion-type dilatation catheter has a short guidewire receiving sleeve or inner lumen extending through a distal portion of the catheter. The structure of the catheter allows for the rapid exchange of the catheter without the need for an exchange wire or adding a guidewire extension to the proximal end of the guidewire. Details of such a rapid exchange type perfusion catheter are disclosed in, for example, U.S. Pat. No. 5,040,548 (Yock) and U.S. Pat. No. 5,061,273 (Yock), which are incorporated by reference herein.

Of interest is U.S. Pat. No. 5,368,566 (Crocker), which discloses a delivery and temporary stent catheter having a reinforced perfusion lumen. The temporary stent in Crocker is used only for maintaining patency of a body lumen while permitting perfusion of fluid through the lumen. Crocker is not directed to delivery of stents after angioplasty procedures.

U.S. Pat. No. 5,222,971 (Willard et al.) discloses a temporary stent for supporting a region of a vessel in a body comprising a stent portion and an actuator portion. The stent portion is comprised of an elongate perfusable vessel supporting portion, wherein the stent provides a flow path radially as well axially or longitudinally.

There is, however, still a need for a stent delivery system that includes a mechanism for perfusing blood during delivery of the stent to the deployment site.

SUMMARY OF THE INVENTION

The present invention is directed to an improved stent delivery system which can quickly and easily position a stent into an occluded region of a blood vessel. In a preferred embodiment, the present invention stent delivery system includes a means for perfusing fluid.

In one preferred embodiment, the present invention is directed to a catheter assembly for maintaining the patency of a body lumen for a period of time sufficient to permit delivery of an expandable stent within the body lumen, comprising an elongated delivery sheath having proximal and distal ends, a sheath lumen extending therein, a first port in the distal end being in fluid communication with the sheath lumen, and at least one sheath perfusion port at the proximal end in fluid communication with the sheath lumen.

The present invention also includes an elongated catheter slidably disposed within the sheath lumen of the sheath, an expandable member proximally adjacent to the distal end of the catheter which receives on the exterior thereof the expandable stent, an inner lumen extending the length of said elongated catheter for receiving a guiding member therein and which extends the entire length of the inner lumen, and at least one catheter perfusion port in the catheter in fluid communication with the inner lumen. The present invention further includes means for adjusting the relative axial positions of the catheter and the sheath to expose the expandable member so that expansion thereof expands the expandable stent.

Preferably, both the delivery sheath and the catheter have slits in the walls thereof which extend distally from their proximal ports to facilitate the rapid removal of these devices from the guidewire upon the withdrawal of the delivery system from the patient's vascular system after the delivery of a stent. The distal end of the delivery sheath may also have slits in the walls thereof which extend a short distance proximally from its distal end to facilitate in the relative axial position adjustment of the delivery sheath and catheter.

In a typical situation, the guidewire used to deliver a dilatation catheter through the patient's vascular system to a stenotic region therein is left within the patient after the dilatation catheter has been removed therefrom. To maintain access to the stenotic region, the distal end of the guidewire should be positioned crossing the stenotic region where the stent is to be placed.

The proximal end of the guidewire, which extends out of the patient, is first inserted through an elastic cone by threading the guidewire into the smaller and out the larger of the two apertures which comprise the cone. Then the guidewire is inserted through the port in the distal end of the intravascular catheter which has a stent mounted on the expandable member. The intravascular catheter is disposed within the delivery sheath with the distal end of the catheter extending out the port in the distal end of the delivery sheath to facilitate the insertion of the proximal end of the guidewire.

The relative axial position between the delivery sheath and intravascular catheter is adjusted so that the expandable member on the distal extremity of the intravascular catheter with the expandable stent mounted thereon is pulled back into the inner lumen of the delivery sheath. The distal end of the delivery sheath is then tucked within the large aperture of the elastic cone. Tucking the delivery sheath within the elastic cone aids the advancement of the stent delivery system through the patient's vascular system by providing the system with a profile suited for making turns through tortuous vessels. The delivery sheath and the catheter therein are then advanced through the patient's vascular system, preferably over a guidewire which extends from outside the patient to the desired coronary artery, until the stent mounted on the expandable member of the intravascular catheter is positioned within the stenotic region of the patients blood vessel.

The relative axial positions of the delivery sheath and the intravascular catheter having the stent thereon is adjusted so that the sheath is withdrawn proximally (in a direction away from the patient) to expose the distal end of the vascular catheter and the expandable stent. As the relative axial positions are adjusted, the cone disengages from the sheath and collapses upon the distal end of the catheter. Once the stent is completely out of the delivery sheath, the expandable member on the intravascular catheter can be expanded to expand the stent against the walls of the blood vessel. After expanding the stent, the expandable member on the vascular catheter is contracted so that the catheter can be removed from the patient's blood vessel, leaving the expanded stent in its desired position therein.

During delivery of the stent to the deployment site, the perfusion ports within the sheath and the catheter provide continuous blood flow via the sheath lumen of the sheath and the inner lumen of the catheter. From the inner lumen, the effluent blood passes through the perfusion ports at the distal end of the catheter to the tissue distal to the catheter. Even as the sheath is withdrawn, the perfusion ports in the sheath enable continuous flow of blood to the perfusion ports in the catheter shaft.

Beneficially, the present invention perfusion ports in the sheath and catheter prevent or minimize ischemic conditions from occurring in the patient. Moreover, the perfusion of blood distal to the inflated balloon allows for long term dilatations.

The delivery sheath and the catheter may be withdrawn together or the sheath may be withdrawn first followed by withdrawal of the catheter. The sheath and the catheter can be peeled away from the guidewire with the guidewire sliding through the slits which extend distally from the proximal ports thereof. The exposed section of the guidewire is secured, e.g., manually held, in place so that the sheath and the intravascular catheter can be pulled off the proximal end of the guidewire.

In one exemplary embodiment of the invention, an over-the-wire catheter system is used to deliver a stent to a location in the vascular system. The over-the-wire catheter includes a proximal shaft and a distal shaft which are retractable in the proximal direction by operation of a sheath retraction switch on a delivery handle. An elongated sheath is at the distal end of the distal shaft and covers and protects the stent and balloon member on the catheter shaft during intravascular delivery. When the sheath retraction switch is moved in the proximal direction, the sheath is caused to move proximally thereby exposing the stent so that it may be deployed.

The delivery system of the invention can effectively deliver a stent to a desired location within a patient's blood vessel, it can allow the stent to be secured within the desired location, and it can be easily and quickly removed. These and other advantages of the present invention will become more apparent from the following detailed description when taken in conjunction with the accompanying exemplary drawings.

BRIEF DESCRIPTION OF THE DRAWINGS

FIG. 1 is a partial longitudinal cross-sectional view of a stent delivery system which embodies features of the invention including perfusion ports in the catheter and sheath.

FIG. 2 is a top view of the delivery sheath with perfusion ports and elastic cone of the stent delivery system shown in FIG. 1.

FIG. 3 is a transverse cross-sectional view taken along the lines 3—3 shown in FIG. 1.

FIG. 4 is a transverse cross-sectional view taken along the lines 4—4 shown in FIG. 1.

FIG. 5 illustrates a stent mounted on the outer surface of a balloon of an exemplary embodiment intravascular catheter such as the one shown in FIG. 1.

FIG. 6 illustrates the advancement of the stent delivery system such as shown in FIG. 5 into an artery which has been damaged by an intravascular procedure such as an angioplasty and the location of the elastic cone prior to the relative axial position adjustment of the delivery sheath and intravascular catheter.

FIG. 7 illustrates the inflation of the balloon on the intravascular catheter shown in FIG. 1 which expands the stent mounted on the exterior thereof and the location of the elastic cone after the relative axial position adjustment of the delivery sheath and intravascular catheter.

FIG. 8 illustrates the expanded stent disposed within a damaged arterial section maintaining the patency thereof.

FIG. 9 is a partial cross-sectional view of the manipulator shown in FIG. 1. FIG. 10 is a perspective view of an alternative manipulator mounted on the proximal end of the delivery system shown in FIG. 1.

FIG. 11 is a plan view of the manipulator shown in FIG. 10.

FIG. 12 is an elevational view, partially in section, of the manipulator shown in FIG. 10.

FIG. 13 is a longitudinal view of a stent delivery system which embodies features of an over-the-wire catheter system.

FIG. 14 is a partial plan view of the delivery sheath of the stent delivery system depicted in FIG. 13 including optional perfusion ports in the sheath.

FIG. 15 is a longitudinal view of a stent delivery system wherein the delivery sheath is depicted in its withdrawn position.

FIG. 16 is a partial plan view of the stent delivery system of FIG. 15 depicting the delivery sheath after it has been withdrawn from the delivery stent.

FIG. 17 is a cross-sectional view of the distal portion of the delivery sheath with perfusion ports as the sheath is partially withdrawn from the stent.

FIG. 18 is a cross-sectional view taken along line 18—18 depicting the distal end of the catheter and elastic cone.

FIG. 19 is a cross-sectional view taken along line 19—19 depicting the sheath in relation to the catheter system.

DETAILED DESCRIPTION OF THE PREFERRED EMBODIMENTS

FIGS. 1–4 illustrate preferred embodiments of a stent delivery system which embodies features of the invention. Generally, the delivery system includes a delivery sheath 10 which has a sheath lumen 11 and a catheter 12 disposed within the sheath lumen 11. As shown in FIG. 1, the delivery sheath 10 preferably includes proximal sheath perfusion ports 1 and distal sheath perfusion ports 2. The perfusion ports 1, 2 are in fluid communication with sheath lumen 11. Their positioning along the sheath 10, of course, may be varied depending upon application. Also, the size, shape, and orientation of the perfusion ports 1, 2 can be changed as needed. For example, the perfusion ports in alternative embodiments may be round holes, vertical slots, horizontal slits, and the like.

The exemplary embodiment intravascular catheter 12 shown in FIG. 1 has an elongated catheter body 13 and a balloon 14 on the distal portion of the catheter body 13. A manipulating device 15 is provided on the distal end of the delivery system which is employed to effect relative axial or longitudinal movement between the delivery sheath 10 and the intravascular catheter 12. An expandable stent 16, which is to be delivered within a patients body lumen, is mounted on the exterior of the balloon 14. During the advancement of the stent delivery system through the patient's vascular system to the region of an occlusion, the sheath 10 is tucked within an elastic cone 58. FIG. 1 shows the location of the elastic cone 58 after the relative axial positions of the sheath 10 and catheter 12 are adjusted to expose the expandable stent 16.

The delivery sheath 10 has a distal port 17 in its distal end which is in fluid communication with the sheath lumen 11 and a proximal port 18 disposed proximally to the distal port. The distal portion of delivery sheath 10 tapers down in a spherical-like manner so that the cross-sectional area is somewhat less in the distal region than the cross-sectional area of the rest of the delivery sheath. A slit 19 extends from the proximal port 18 to a location just proximal to the distal port 17. In one embodiment, a plurality of slits 59 in the wall of sheath 10 extend a short distance from the distal port 17.

As contemplated, the slits 59 would facilitate in the relative axial position adjustment of the sheath 10 and intravascular catheter 12.

The intravascular catheter 12 has a distal port 20 and a proximal port 21 which are in fluid communication with a first inner lumen 22 extending within the distal portion of the catheter 12 and being adapted to slidably receive a guidewire therein. A slit 23 extends from the proximal port 21 to a location 24 proximal to the proximal end of balloon 14. The proximal end of the guidewire receiving first inner lumen 22 is provided with a ramp 25 to guide the proximal end of guidewire 26 out the proximal port 21 of intravascular catheter 12 when the catheter is mounted onto the guidewire, as will be discussed hereinafter. A second, much longer inner lumen 27 is provided within the catheter body 13 to direct inflation fluid from the proximal end of the catheter body to the interior of the balloon 14.

At least one optional catheter perfusion port 3 is located at a proximal portion of the catheter body 13, and is in fluid communication with the first inner lumen 22. Thus, blood flows through the sheath perfusion ports 1, 2, then through the sheath lumen 11, and ultimately through the catheter perfusion port 3 into the first inner lumen 22. The blood passes through distal port 20 or through optional perfusion ports at the distal end of the catheter body 13 to supply the tissue distal from the balloon 14.

Proximal to the proximal port 21 in the catheter body 13 is a stiffening member 28 which is disposed in third inner lumen 29 provided within the catheter body 13. As shown in the drawings, the third inner lumen 29 and the first inner lumen 22 may be the same lumen with a plug 30 separating the two lumens. The ramp 25 is on the distal side of the plug 30.

As illustrated in FIGS. 1 and 9, the manipulator 15 on the proximal end of the delivery system has a housing 31 with an interior chamber 32, a cap 33 rotatably mounted onto the distal end of the housing 31, an elongated drive member 34 which has male threads on the exterior thereof and which is at least partially disposed within the interior chamber 32 and a Luer lock 35 which is fixed within the proximal end of the housing 31. The proximal end 36 of the sheath 10 is secured to the distal end 37 of the elongated drive member 34 which extends out of the distal end of the housing 31. As shown in more detail in FIG. 9, the proximal end 38 of the catheter body 13 passes through passageway 39 in the elongated drive member 34 and is fixed within the Luer lock 35 by suitable means such as adhesive. The cap 33 which is rotatably mounted onto the distal end of the housing 31 is provided with an inner threaded collar 40 adapted to threadably engage the threaded exterior of the elongated driving member 34. Rotation of the cap 33 moves the driving member 34 axially to thereby effect relative axial movement between the sheath 10 and the intravascular catheter 12. As can be seen from FIGS. 1 and 6, the sheath lumen 11 is axially spaced from catheter 12, at inner lumen 27, in a substantially non-abutting manner. Thus when the delivery sheath 10 overlies the intravascular catheter 12, there is little or no contact present at the interface between the sheath lumen 27 proximal to the distal end of intravascular catheter 12.

In a typical situation, the stent delivery system of the present invention is used after an intravascular procedure has damaged a patient's arterial lining to such an extent that the lining needs support to prevent it from collapsing into the arterial passageway and thereby preventing sufficient blood flow through the blood vessel. In these situations, there is usually a guidewire 26 (or other guiding member) in place extending across the damaged section of the artery such as shown in FIG. 6. The proximal end of the guidewire 26, which extends out of the patient during the entire procedure, is inserted through the elastic cone 58 by threading the guidewire 26 into the small aperture 61 and out the large aperture 60 of the cone 58. The guidewire 26 is then inserted through the distal port 20 in the distal end of the catheter 12 and advanced proximally through the first inner lumen 22 until the proximal end of the guidewire impacts the ramp 25 and is thereby directed through the proximal port 21.

The catheter assembly 12 is preferably positioned within the sheath lumen 11 of the delivery sheath 10 so that at least a significant portion of the proximal port 18 in the sheath is in alignment with the proximal port 21 of the intravascular catheter. In this manner, proximal advancement of the guidewire 26 through the inner lumen 22 will also direct the proximal end of the guidewire out the proximal port 18 in the delivery sheath 10. The sheath 10 is then tucked within the elastic cone 58 by inserting the distal end of sheath 10 into the proximal end and large aperture 60 of the cone 58. The proximal end of the guidewire 26 may then be manually held to maintain the position of the guidewire within the patient's vasculature, while the stent delivery system is advanced over the guidewire and through the patient's vascular system.

A function of the elastic cone 58 is to facilitate the advancement of the stent delivery system. By tucking the distal end of sheath 10 within the cone 58 as shown in FIG. 6, the stent delivery system has a profile suited for successfully maneuvering about the sharp turns and angles of the patient's vasculature.

The advancement of the stent delivery system continues until the distal ends of the catheter and sheath extend adjacent to or across the damaged arterial site. Next, the manipulator 15 on the proximal end of the delivery system is actuated by rotating the cap 33 on the proximal end of the housing 31 to move the sheath 10 proximally with respect to the catheter 12 and thereby expose the stent 16 mounted on the balloon 14. The elastic cone 58 disengages the sheath 10 and collapses in engagement about the distal portion of the catheter 12 as is shown in FIG. 1.

When the balloon and the stent mounted thereon are properly placed within the damaged artery, inflation fluid is directed under substantial pressure through the Luer lock 35 and the inflation lumen 27 in the catheter body 13 to the interior of the balloon 14, expanding the balloon and simultaneously expanding the stent 16 against the blood vessel wall as shown in FIG. 7. The delivery system, both the sheath 10 and the catheter 12, may then be removed from the patient along with the guidewire 26, leaving the expanded stent 16 within the damaged arterial section as shown in FIG. 8 to maintain the patency thereof.

The housing 31 of the manipulator 15 can be held in the palm of the physician's hand, with the thumb and index finger thereof used to rotate cap 33 and thereby cause the necessary relative motion between the sheath 10 and intravascular catheter 12 to expose the stent 16 mounted on the balloon 14. The physician can operate an inflation device, such as described in U.S. Pat. No. 4,439,185, with his or her free hand to inject inflation fluid through Luer lock 35 into the interior of the balloon 14 to inflate the balloon and thereby expand the stent 16 while holding the delivery system in place with the other hand. Upon deflating the balloon 14, the manipulator 15 can again be actuated by the physician rotating cap 33 with the fingers of the hand holding the manipulator 15, to cause relative rotation between the intravascular catheter 12 and the sheath 10, to pull the intravascular catheter 12 back into the distal end of the sheath 10 (or pushing the distal end of the sheath over the distal end of the intravascular catheter 12, depending upon the perspective) The entire assembly, including the guidewire 26, can then be removed from the patient.

The alternative manipulator 50 illustrated in FIGS. 10–12 generally includes a housing 51 with an interior chamber 52 and a slidable element 53 with a depending portion 54 which extends through a slot 55 in the wall of the housing and is secured to the proximal end of the sheath 10 which extends through an opening provided in the distal end of the housing. The catheter 12 extends out the proximal end of the sheath 10, out an opening in the proximal end of the housing 51 and into a Luer lock 56 secured to the proximal end of the housing. The proximal end of the catheter 12 is secured within the Luer lock 56 to be in fluid communication with the inner inflation lumen 27 of the catheter so that inflation fluid can be injected through the Luer lock to the interior of the balloon 14 on the catheter to expand the balloon and the stent 16 mounted thereon. As is evident from FIG. 10, movement from element 53 on the exterior of the housing 51 will effect the relative axial movement between the delivery sheath 10 and the catheter 12 required to expose the stent 16 mounted on the balloon 14. The slot 55 has narrowed portions near both ends thereof which have widths just slightly smaller than the depending element 54 so that the position of the slidable element 53 can be locked. The underside of the housing 51 may be provided with undulated surface 57 which is adapted to receive the fingers of an operator to facilitate the gripping thereof.

In another exemplary embodiment of the invention, as depicted in FIGS. 13–19, an over-the-wire catheter system is employed to carry the sheath and the stent within the patient's vasculature to the damaged area. A guidewire 26 is employed to cross a damaged area and locate the position within the patient so that the intravascular catheter 12 can reach the area.

As is typical in over-the-wire catheter systems, the intravascular catheter 12 has an outer member 77 and an inner member 78 which are coaxially aligned. Inner member 78 has an inner lumen 79 which carries guidewire 26. The guidewire can move freely within inner lumen 79 in an axial direction.

In keeping with the invention, as depicted in FIGS. 13–19, sheath 10 is located at the distal end of distal retractable sheath 74. Catheter assembly 12 is slidably disposed within sheath 10 in inner lumen 11. Port 17 at the distal end of sheath 10 provides an opening for catheter 12 to extend.

Sheath 10 has a flared portion or expanded portion located at the distal end of distal retractable sheath 74. It is contemplated that sheath 10 can be formed from the same shaft as distal retractable sheath 74, or can be a separate member (not shown) attached to the distal end of distal retractable sheath 74. The flared or enlarged diameter portion of sheath 10 must large enough to accommodate the underlying balloon 14 and expandable stent 16. It is also contemplated that sheath 10 would not have a flared portion as depicted in order to reduce the profile of sheath 10.

Notch 80 at the distal end of sheath 10 is incorporated to provide a softer and more flexible distal end to sheath 10. When the intravascular catheter 12 is being urged through the patient's vasculature, a softer distal end of sheath 10 is desirable, and notch 80 provides flexibility and the required softness. More than one notch is contemplated to further increase flexibility and softness in the distal end of sheath 10. If a stiffer, less flexible end is desired, sheath 10 can be provided without any notch 80.

Distal retractable sheath 74 is connected to proximal retractable sheath 75 which is a somewhat larger diameter and a stiffer member, than distal retractable sleeve 74. Thus, the distal end of the sheath will have more flexibility than the proximal end. It is also contemplated that the invention could incorporate a retractable sheath having only one diameter along its length to provide uniform stiffness throughout.

An elastic cone 58 is attached to intravascular catheter 12 near its distal tip. Elastic cone 58 has a large aperture 60 which is elastic enough to overlay the very distal end of sheath 10. The elastic cone also has a small aperture 61 at its distal end which is attached to outer member 77 by known methods such as heat shrinking or adhesive. The elastic cone 58 is intended to provide a covering over the distal end of sheath 10 as the sheath moves through the tortuous vasculature and will prevent sheath 10 from getting caught in the vasculature.

Furthermore, the intravascular catheter 12 includes optional catheter perfusion ports 5 at a distal end thereof. The catheter perfusion ports 5 are in fluid communication with the inner lumen 79 that carries guidewire 26. An influx of blood may optionally be supplied to the distal perfusion port 5 through the inner lumen 79, from a blood supply source 6, as is known in the art of perfusion catheters.

In addition, the preferred embodiment sheath 10 includes sheath perfusion ports 4, shown in FIGS. 14 and 16 as horizontal slots. Alternatively, the ports 4 may be vertical slots. Of course, the size, shape, location, and orientation of the ports 4 may be changed as needed. The perfusion ports 4 enable blood flow through the sheath 10. The sheath perfusion ports 4 are useful in one alternative embodiment of the catheter having proximal perfusion ports (not shown). Specifically, as the sheath 10 is retracted, the sheath perfusion ports 4 ensure continuous blood flow in the event those proximal catheter perfusion ports are covered or blocked by the retracting sheath 10.

A blood supply 6 that is known in the art directs blood through inner lumen 79. The blood flows through inner lumen 79 and out catheter perfusion port 5 to the tissue distal from the catheter 12.

As described above, sheath 10 provides a protective cover for stent 16 while the stent is being transported through the patient's vasculature. Once the damaged area has been crossed, the stent is then ready to be deployed.

In order to deploy the stent, a manipulator handle 70 is utilized to retract sheath 10. The proximal end (not shown) of proximal retractable sheath 75 is attached to connector 72. A sheath retraction switch 71 is operated by the physician's thumb by moving the switch in the proximal direction. Sheath retraction switch 71 is attached to connector 72 which is slidably mounted in elongated slot 73. As sheath retraction switch 71 is moved in the proximal direction, proximal retractable sheath 75 and distal retractable sheath 74 also move in the proximal direction. Since sheath 10 is connected to distal retractable sheath 74 it too moves in the proximal direction a sufficient distance to expose stent 16 and balloon 14. It is preferred to position a radiopaque marker 67 near the distal end of sheath 10 so that the physician can determine when sheath 10 has been withdrawn a sufficient distance so as not to interfere with the deployment of stent 16. Alternatively, the radiopaque marker can be positioned at location 68 (FIG. 14) rather than at radiopaque marker 67. When radiopaque marker 68 is positioned on distal retractable sheath 74, it has a lower profile than radiopaque marker 67, thus allowing sheath 10 to cross an occluded area more easily.

In order to deploy stent 16, the balloon 14 is inflated with an inflation fluid through inflation port 65. As shown in FIG. 17, an inflation fluid supply 7, known in the art, directs inflation fluid into balloon 14. After stent 16 has been deployed, balloon 14 is deflated and the intravascular catheter 12 is removed from the patient's vasculature.

In the preferred embodiment of the present invention, the dimensions of the intravascular catheter generally follows the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm and the inflated diameter about 1 mm to about 8 mm.

The materials of construction may be selected from those used in conventional balloon angioplasty catheters, such as those described in the patents incorporated by reference. The delivery sheath will generally be slightly shorter than the intravascular catheter, e.g., by about the length of the manipulating device 15 or 50, with an inner diameter large enough to accommodate the intravascular catheter and to allow the catheter free longitudinal movement therein. The sheath and the catheter shaft can be made of conventional polyethylene tubing.

While the present invention has been described herein in terms of delivering an expandable stent to a desired location within a patient's blood vessel, the delivery system can be employed to deliver stents to locations within other body lumens such as urethra or Fallopian tubes so that the stents can be expanded to maintain the patency of these body lumens. Various changes and improvements may also be made to the invention without departing from the scope thereof.

What is claimed is:

1. A catheter assembly for maintaining the patency of a body lumen for a period of time sufficient to permit delivery of an expandable stent within the body lumen, comprising:

an elongated sheath having proximal and distal ends, a sheath lumen extending therein, a first port in the distal end being in fluid communication with the sheath lumen, and at least one sheath perfusion port in the sheath in fluid communication with the sheath lumen;

an elongated catheter disposed within the sheath lumen and having a proximal and a distal end wherein the catheter includes at least one catheter perfusion port, the elongated catheter having an outer member and an inner member, an expandable member proximally adjacent to the distal end of the outer member receiving the expandable stent on the exterior thereof, an inner lumen within, and extending the length of said inner member and receiving a guiding member therein along the entire length of the inner lumen, the inner lumen also being in fluid communication with the catheter perfusion port; and means for adjusting the relative axial positions of the catheter and the sheath to expose the expandable member so that expansion thereof expands the expandable stent, and permits blood flow through the first port in the sheath and the at least one catheter perfusion port.

2. A system for the delivery of an expandable stent within a body lumen over a guiding member comprising:

an elongated sheath having proximal and distal ends, a sheath lumen extending therein, a first port in the distal end of said sheath being in fluid communication with the sheath lumen, and a perfusion port in the sheath in fluid communication with the sheath lumen;

an elongated catheter slidably disposed within the sheath lumen, an expandable member proximally adjacent to the distal end of the catheter receiving on the exterior thereof the expandable stent, an inner lumen extending the length of said elongated catheter for receiving the guiding member therein along the entire length of the inner lumen, and at least one catheter perfusion port in the catheter in fluid communication with the inner lumen; and means for adjusting the relative axial positions of the catheter and sheath to expose the expandable member and the stent.

3. The stent delivery system of claim 2, wherein the sheath has a tapered portion on the distal end.

4. A catheter assembly for maintaining the patency of a body lumen for a period of time sufficient to permit delivery of an expandable stent within the body lumen, comprising:

an elongated sheath having a proximal end and a distal end, a flared portion proximal to the distal end, a tapering portion proximal to the flared portion, a sheath lumen extending therein, a first port in the distal end and a second port at the proximal end, both of the ports being in fluid communication with the sheath lumen, and at least one sheath perfusion port in the sheath in fluid communication with the sheath lumen;

an elongated catheter slidably disposed within the sheath lumen, an expandable member proximally adjacent to the distal end of the catheter receiving on the exterior thereof the expandable stent, an inner lumen extending the length of said elongated catheter for receiving a guiding member therein and along the entire length of the inner lumen, and at least one catheter perfusion port in the catheter in fluid communication with the inner lumen;

an elastic cone having a proximal end and a distal end and having a small aperture in the distal end and a large aperture in the proximal end thereof, the large aperture receiving the distal end of the elongated sheath; and a manipulator handle having a switch adapted to move axially in the handle, the switch attached to the proximal end of the sheath so that as the switch is moved proximally the sheath moves proximally to expose the stent and the expandable member.

5. The catheter as defined in claim 4, wherein the sheath perfusion port includes a plurality of vertical slots.

6. The catheter as defined in claim 4, wherein the sheath perfusion port includes a plurality of horizontal slots.

7. The catheter as defined in claim 4, wherein the catheter perfusion port includes a plurality of slots.

8. The catheter as defined in claim 4, wherein the sheath perfusion port is located at the distal end of the sheath.

9. A method of delivering an expandable stent to a desired location within a patient's body lumen which has a guidewire disposed therein with a proximal end extending out of the patient, the method comprising the steps of:

providing an elongated sheath with a sheath lumen therein and a sheath perfusion port in fluid communication with the sheath lumen, the sheath having proximal and distal ends, and a first port in the distal end of the sheath;

providing an elongated catheter disposed within the elongated sheath, the catheter having an expandable member proximally adjacent to the distal end of the catheter and having mounted on the exterior thereof the expandable stent, the catheter having an inner lumen extending the length of the cather and adapted to slidably receive a guidewire therein along the entire length of the inner lumen, wherein the catheter further includes a catheter perfusion port in fluid communication with the inner lumen;

advancing the sheath and catheter over the proximal end of the guidewire and through the body lumen to the desired location therein;

adjusting the relative axial position of said sheath with respect to said catheter to expose the expandable stent on the expandable member;

expanding the expandable member to expand the stent mounted thereon at the desired location within the body lumen;

contracting the expandable member on the catheter; and withdrawing the catheter and sheath from the body lumen.

10. The method of claim 9, wherein the expandable member includes a balloon and wherein an inflation fluid is directed to the interior of the balloon to expand the balloon and thereby expand the stent mounted thereon.

11. The method of claim 9, wherein the method further comprises the step of perfusing a fluid through the sheath perfusion port.

12. The method of claim 9, wherein the step of providing an elongated sheath includes a sheath having a plurality of perfusion ports.

* * * * *